(12) United States Patent
Miyake et al.

(10) Patent No.: US 8,834,442 B2
(45) Date of Patent: Sep. 16, 2014

(54) DIAPER COVER AND DISPOSABLE DIAPER

(75) Inventors: Hirofumi Miyake, Mima-gun (JP);
Akiko Tatsukawa, Mima-gun (JP);
Saeko Okuto, Osaka (JP)

(73) Assignee: Livedo Corporation, Ehime (JP)

( * ) Notice: Subject to any disclaimer, the term of this patent is extended or adjusted under 35 U.S.C. 154(b) by 0 days.

(21) Appl. No.: 13/577,728

(22) PCT Filed: Apr. 12, 2011

(86) PCT No.: PCT/JP2011/002146
§ 371 (c)(1),
(2), (4) Date: Aug. 8, 2012

(87) PCT Pub. No.: WO2011/129097
PCT Pub. Date: Oct. 20, 2011

(65) Prior Publication Data
US 2012/0316535 A1  Dec. 13, 2012

(30) Foreign Application Priority Data

Apr. 14, 2010 (JP) .................................. 2010-093573
Jun. 9, 2010 (JP) .................................. 2010-132456

(51) Int. Cl.
*A61F 13/15* (2006.01)
*A61F 13/62* (2006.01)
*A44B 18/00* (2006.01)
*A61F 13/56* (2006.01)

(52) U.S. Cl.
CPC ........... *A61F 13/625* (2013.01); *A44B 18/0061* (2013.01); *A61F 2013/5688* (2013.01); *A61F 13/5622* (2013.01)
USPC ........................................... 604/391; 24/442

(58) Field of Classification Search
CPC .......................... A61F 13/625; A44B 18/0061
USPC ............................. 604/391; 24/442, 450, 452
See application file for complete search history.

(56) References Cited

U.S. PATENT DOCUMENTS 5,300,058 A   4/1994   Goulait et al.
5,669,901 A   9/1997   LaFortune et al.
(Continued)

FOREIGN PATENT DOCUMENTS

EP   0 528 282   8/1992
EP   2 289 474   3/2011
(Continued)

OTHER PUBLICATIONS

Office Action issued Apr. 4, 2013 in corresponding Australian Application No. 2011241721.

(Continued)

*Primary Examiner* — Melanie Hand
*Assistant Examiner* — Aundria Hairell
(74) *Attorney, Agent, or Firm* — Wenderoth, Lind & Ponack, LLP

(57) ABSTRACT

A diaper cover having a front part, a back part and an intermediate part located between the front part and the back part in a front-back direction, a right waist part and a left waist part extending from the back part in a width direction, and a right flap part and a left flap part extending from the front part in the width direction. The right flap part and/or the left flap part is provided with a hook member having a plurality of hooks. The hook member has a first region in which the hooks are oriented in one direction and a second region in which the hooks are oriented in another direction; and the first region and the second region are arranged such that a hypothetical straight line extending in the front-back direction in the right flap part or the left flap part crosses both the first region and the second region.

8 Claims, 8 Drawing Sheets

(56) References Cited

U.S. PATENT DOCUMENTS

| | | |
|---|---|---|
| 5,884,374 A | 3/1999 | Clune |
| 2003/0100879 A1* | 5/2003 | Kline et al. .................. 604/386 |
| 2003/0120251 A1* | 6/2003 | Couture et al. ............... 604/391 |
| 2007/0039142 A1 | 2/2007 | Petersen et al. |
| 2011/0066129 A1 | 3/2011 | Kinoshita et al. |

FOREIGN PATENT DOCUMENTS

| | | |
|---|---|---|
| JP | 2000-508930 | 7/2000 |
| JP | 2002-524171 | 8/2002 |
| JP | 2003-190213 | 7/2003 |
| JP | 2006-42863 | 2/2006 |
| JP | 2006-141535 | 6/2006 |
| JP | 2006-527021 | 11/2006 |
| JP | 2009-273730 | 11/2009 |
| WO | 97/36566 | 10/1997 |
| WO | 00/15069 | 3/2000 |
| WO | 02/14701 | 2/2002 |

OTHER PUBLICATIONS

International Search Report issued Jul. 19, 2011 in corresponding International Application No. PCT/JP2011/002146.

Notice of Reasons for Rejection issued Nov. 26, 2013 in Japanese corresponding patent application No. 2010-132456.

Australian Office Action issued Oct. 16, 2013 in corresponding Australian patent application No. 2011241721.

Office Action issued May 20, 2014, in corresponding Japanese Application No. 2010-132456 (with English translation).

Office Action issued Feb. 8, 2014, in corresponding Chinese Application No. 201180008333.3 with English tranlsation.

Office Action issued Jun. 13, 2014 in corresponding European patent application No. 11720893.4.

* cited by examiner

DIAPER COVER AND DISPOSABLE DIAPER

BACKGROUND OF THE INVENTION

1. Technical Field

The present invention relates to a diaper cover and a disposable diaper.

2. Description of the Related Art

Conventionally, there is known a diaper cover comprising a front part, a back part and an intermediate part located therebetween in a front-back direction, a right waist part and a left waist part extending from the back part in a width direction, and a right flap part and a left flap part extending from the front part in the width direction. In such a diaper cover, the right waist part and the left waist part are applied around the waist of a wearer, and then, the right flap part and the left flap part are joined to the right waist part or the left waist part which have been applied around the waist of the wearer, whereby the diaper cover can be worn. For example, Japanese Patent Application Laid-Open Publication No. 2006-42863 discloses such a diaper cover, which further comprises hook members of a hookand-loop fastener provided in at least one of the right waist part and the left waist part and both of the right flap part and the left flap part.

SUMMARY OF THE INVENTION

1. Technical Problem

In the diaper cover disclosed in JP 2006-42863, the hook member provided at the flap part is often joined to a position about the pelvis (that is, the ilium, particularly the iliac crest or the like) of a wearer when the diaper cover is worn. In such a part of a human body, a great uneven or curved surface is found, and therefore, when the hook member is joined to such a position, the hook member is easily disjoined.

The present invention has been achieved in view of the above circumstances, and an object of the present invention is to provide a diaper cover and a disposable diaper in which a hook member provided at a flap part is less likely to be disjoined.

2. Solution to the Problem

A diaper cover of the present invention which solves the above problems comprises a front part, a back part and an intermediate part located between the front part and the back part in a front-back direction, a right waist part and a left waist part extending from the back part in a width direction, and a right flap part and a left flap part extending from the front part in the width direction, wherein: the right flap part and/or the left flap part is provided with a hook member having a plurality of hooks; the hook member has a first region in which the hooks are oriented in one direction and a second region in which the hooks are oriented in another direction; and the first region and the second region are arranged such that a hypothetical straight line extending in the front-back direction in the right flap part or the left flap part crosses both the first region and the second region.

In the diaper cover of the present invention, since the hooks of the hook member are oriented in different directions in the first region and in the second region, joining (engaging) of both the first region and the second region are less likely to be disjoined at one time even when forces acting in various directions are applied to the hook member in the flap part (the right flap part and/or the left flap part). Further, in the diaper cover, since the first region and the second region are arranged such that a hypothetical straight line extending in the front-back direction in the right flap part or the left flap part crosses both the first region and the second region, the first region and the second region easily fit an uneven or curved surface of a wearer in an up-down direction of the wearer even when the hook member is joined to a position about the pelvis (that is, the ilium, particularly the iliac crest or the like) of the wearer. As a result, the hook member can be stably fixed around the waist of a wearer in wearing the diaper cover.

Preferably, the right flap part and/or the left flap part is provided with the plurality of hook members including a first hook member having the first region and a second hook member having the second region, and the first hook member and the second hook member are arranged such that the hypothetical straight line crosses both the first hook member and the second hook member. When the first region and the second region are formed in different hook members like this, joining of the hook member provided at the flap part is strengthened. In addition, it becomes easy to form the first region and the second region in the flap part.

It is preferable that the first hook member narrows inward in the width direction in the right or left flap part, and the second hook member narrows outward in the width direction in the right or left flap part. When the first hook member and the second hook member are provided in this manner, the first hook member can resist against a peeling force from the end side of the right or left flap part, and the second hook member can resist a peeling force from the inner side of the right or left flap part. Specifically, the second hook member is less likely to be disjoined to the right and left flap part even when the front part of the diaper cover is distorted or twisted due to a wearer's heavy movement. In addition, since the first hook member and the second hook member can be arranged close to each other, the total area of the hook members is easily enlarged. As a result, a total joining force of the hook members is easily improved.

It is also preferable that each of the first hook member and the second hook member narrows inward from an edge of the right or left flap part. When the first hook member and the second hook member are provided in this manner, the first hook member and the second hook member can respectively resist a peeling force from the edge of the right or left flap part, and therefore, joining of each the first hook member and the second hook member is strengthened. In addition, since the first hook member and the second hook member can be arranged close to each other, the total area of the hook members is easily enlarged. As a result, a total joining force of the hook members is easily improved.

It is also preferable that each of the first hook member and the second hook member narrows inward in the width direction in the right or left flap part. When the first hook member and the second hook member are provided in this manner, the first hook member and the second hook member can respectively resist a peeling force from the end side of the right or left flap part, and therefore, joining of each the first hook member and the second hook member is strengthened. Moreover, since the first hook member and the second hook member narrow inward in the width direction, flexibility and stretchability of the diaper cover are less likely to be inhibited by the hook member at the inner side, with respect to the width direction, of the right or left flap part, thereby improving handleability of the diaper cover.

The first hook member and the second hook member are preferably separated from each other. When the hook members are provided so as to be separated from each other, a portion of the flap part where the hook members are provided easily fits an uneven or curved surface of a wearer. In addition, all joining of the hook members provided at the flap part becomes less likely to be disjoined at one time.

The right flap part, the left flap part and the intermediate part are preferably stretchable. When the diaper cover is stretchable at these parts, fitting property of the diaper cover around the legs of a wearer is easily improved by fixing the right and left flap parts to the abdomen side of the wearer while the right and left flap parts being expanded in the right-left direction of the wearer and being pulled in the upward direction of the wearer.

One or both of the right waist part and the left waist part is preferably provided with a waist attachment. When the waist attachment is provided, the right and left waist parts are easily fixed around the waist of a wearer.

The present invention also provides a disposable diaper in which an absorbent core is provided at the intermediate part of the diaper cover of the present invention. Also in the disposable diaper of the present invention, the hook member can be stably fixed around the waist of a wearer in wearing the disposable diaper.

3. Advantageous Effects of Invention

In the diaper cover and the disposable diaper of the present invention, the hook member provided at the flap part is less likely to be disjoined in wearing the diaper cover or the disposable diaper.

DETAILED DESCRIPTION OF THE EMBODIMENTS

Figure 1:
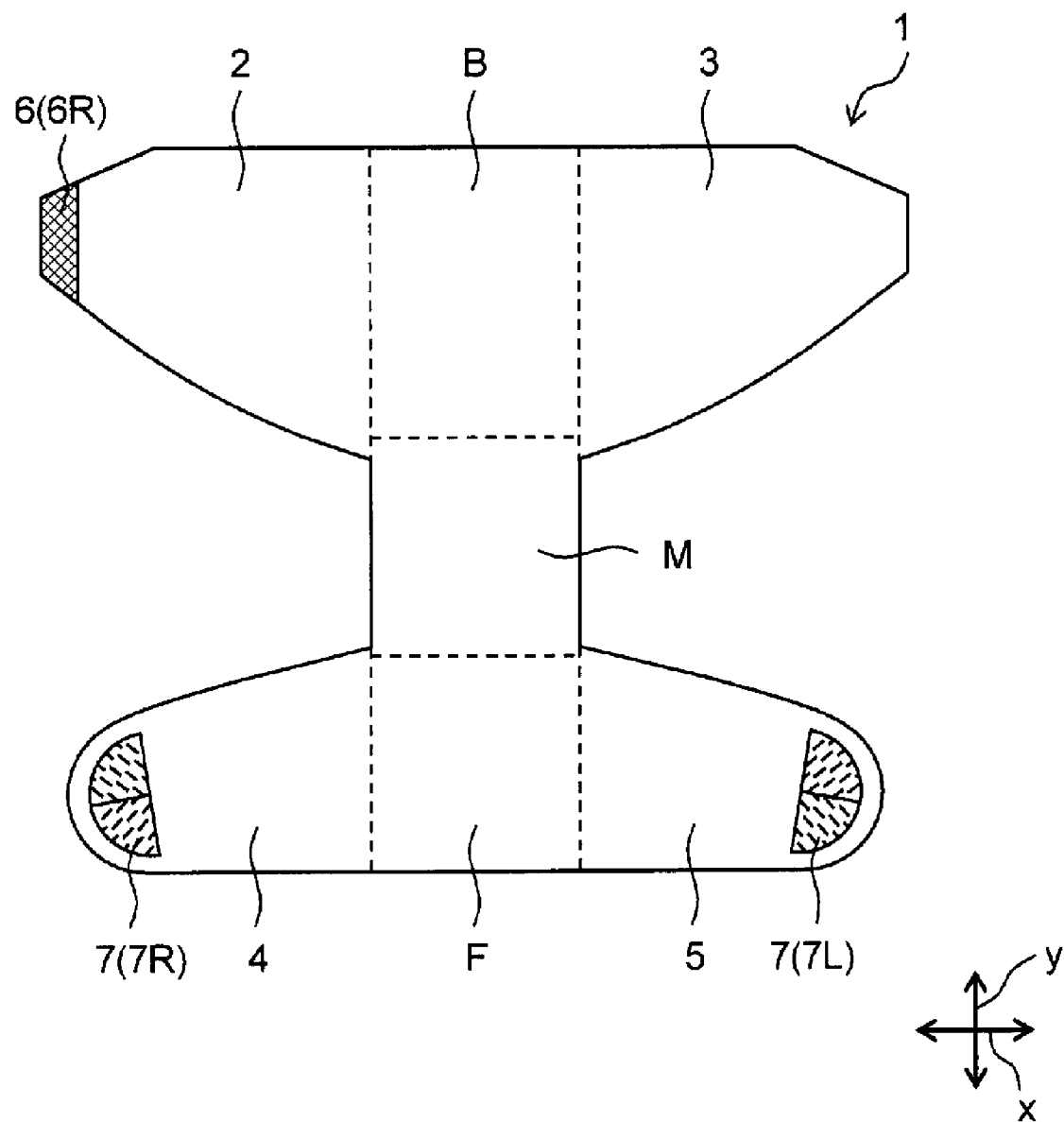
FIG. 1 shows one embodiment of a diaper cover of the present invention.

A diaper cover of the present invention is explained referring to the drawings. However, the diaper cover of the present invention is not restricted to the embodiments shown in the drawings. FIG. 1 shows an example of the diaper cover of the present invention. In the drawings, the arrow x represents a width direction, and the arrow y represents a front-back direction.

A diaper cover 1 has a front-back direction y and a width direction x. The front-back direction y means a direction extending in a front-back direction at a crotch of a wearer when the wearer wears the diaper cover. In FIG. 1, a lower side of the drawing corresponds to a front side of the diaper cover, and an upper side of the drawing corresponds to a back side of the diaper cover. The width direction x means a direction orthogonal to the front-back direction y on the same plane as the diaper cover. The width direction x corresponds to a direction extending in a right-left direction of a wearer when the wearer wears the diaper cover. The diaper cover 1 also has an inner side located on a wearer's side and an outer side located on an opposite side of the wearer in wearing the diaper cover.

The diaper cover 1 comprises a front part F, a back part B and an intermediate part M located therebetween in the front-back direction y. The front part F is formed at one end of the diaper cover 1 in the front-back direction y, and means a portion applied to an abdomen side of a wearer when the diaper cover is worn. The back part B is formed at the other end of the diaper cover 1 in the front-back direction y, and means a portion applied to a dorsal side of the wearer when the diaper cover is worn. The intermediate part M is positioned between the front part F and the back part B, and means a portion applied to a crotch of the wearer when the diaper cover is worn. In the present invention, it is defined that the front part F, the back part B and the intermediate part M are parts excluding a right waist part 2, a left waist part 3, a right flap part 4 and a left flap part 5 described below. In FIG. 1, the front part F, the intermediate part M, the back part B, the right waist part 2, the left waist part 3, the right flap part 4 and the left flap part 5 are shown so as to be sectioned from each other by dashed lines, conveniently.

For example, the front part F, the intermediate part M and the back part B occupy portions equivalent to 30%, 30%, and 40%, respectively, of the length of the diaper cover 1 in the front-back direction y. The diaper cover 1 shown in FIG. 1 is divided into the front part F, the intermediate part M and the back part B in such a ratio.

The diaper cover 1 comprises the right waist part 2 and the left waist part 3 extending from the back part B in the width direction x. The right waist part 2 and the left waist part 3 are portions applied to a right side and a left side, respectively, of a waist of a wearer in wearing the diaper cover. In FIG. 1, a right side of the drawing corresponds to a left side of a wearer and a left side of the drawing corresponds to a right side of the wearer in wearing the diaper cover. Thus, the diaper cover of FIG. 1 is shown such that the inner side of the diaper cover is seen.

The diaper cover 1 is formed such that the intermediate part M is the narrowest in the width direction x. The right waist part 2 and the left waist part 3 correspond to portions located outward from outer edges of the narrowest part of the intermediate part M in the width direction x. The right waist part 2 and the left waist part 3 extend at least from the back part B in the width direction x, and may extend further from the intermediate part M in the width direction x. The diaper cover 1 covers the waist of a wearer with the right waist part 2, the left waist part 3 and the back part B when the diaper cover 1 is worn. It is preferred that the diaper cover 1 is worn such that the length of a portion where the right waist part 2 and the left waist part 3 overlap each other in the width direction x is about 10% or more and about 60% or less (more preferably about 20% or more and about 50% or less) of a waist circumference length of a wearer.

The diaper cover 1 comprises the right flap part 4 and the left flap part 5 extending from the front part F in the width direction x. The right flap part 4 and the left flap part 5 correspond to portions located outward from the outer edges of the narrowest part of the intermediate part M in the width direction x. The right flap part 4 and the left flap part 5 extend at least from the front part F in the width direction x, and may extend further from the intermediate part M in the width direction x. The right flap part 4 and the left flap part 5 are portions which cover the abdomen of a wearer with the front part F when the diaper cover 1 is worn. The right flap part 4 and the left flap part 5 may be allowed to reach to the dorsal side of a wearer when the diaper cover 1 is worn.

One or both of the right waist part 2 and the left waist part 3 is preferably provided with a waist attachment 6. When one or both of the right waist part 2 and the left waist part 3 is provided with a waist attachment 6, the right waist part 2 and the left waist part 3 can be connected to each other by the waist attachment 6, whereby the right and left waist parts 2, 3 are easily fixed around the waist of a wearer. Hereinafter, a reference sign "6R" may be used for representing the waist attachment provided at the right waist part, and a reference sign "6L" may be used for representing the waist attachment provided at the left waist part. FIG. 1 shows an embodiment in which only the waist attachment 6R is provided at the right waist part 6, and in such a diaper cover, the right and left waist parts 2, 3 can be fixed around the waist of a wearer by joining the right waist part 2 to the left waist part 3 or the back part B with the waist attachment 6R.

The right flap part 4 and/or the left flap part 5 is provided with a hook member 7 having a plurality of hooks. In FIG. 1, each of the right flap part 4 and the left flap part 5 is provided with a hook member 7. As the hook member 7, a hook member of a hook-and-loop fastener can be used. Hereinafter, a reference sign "7R" may be used for representing the hook fastener provided at the right flap part, and a reference sign "7L" may be used for representing the hook fastener provided at the left flap part.

The hook members 7 of the right and left flap parts 4, 5 are preferably provided so as to be attachable to the outer surface (the surface located on the outer side) of the right waist part 2, the left waist part 3 or the back part B. Thus, the hook members 7 are preferably provided on the inner surfaces of the right and left flap parts 4, 5.

For wearing the diaper cover 1, the right and left flap parts 4, 5 are joined to the right waist part 2, left waist part 3 or the back part B, which has been applied around the waist of a wearer, by the hook members 7. As a result, the diaper cover 1 is applied tightly around the waist of the wearer, thereby enhancing the fitting property of the diaper cover 1. Specifically, the fitting property about the inguinal region on the right side of a wearer is enhanced by edges of the right waist part 2, the right side of the intermediate part M, and the right flap part 4; and the fitting property about the inguinal region on the left side of a wearer is enhanced by edges of the left waist part 3, the left side of the intermediate part M, and the left flap part 5.

Preferably the hook member 7 is provided at the right flap part 4 and/or the left flap part 5 so as to be attachable to a position on the dorsal side or the lateral side of a wearer. Specifically, the hook member 7 is preferably attachable to a position as far as 5% or more and 35% or less of the waist circumference length of a wearer away from the backbone (specifically, a centerline of the backbone) of the wearer, that is a region corresponding to 60% of the waist circumference length in all of right and left sides of a wearer. The centerline of the backbone means a centerline extending vertically in the state where the wearer stands.

Figure 2A:
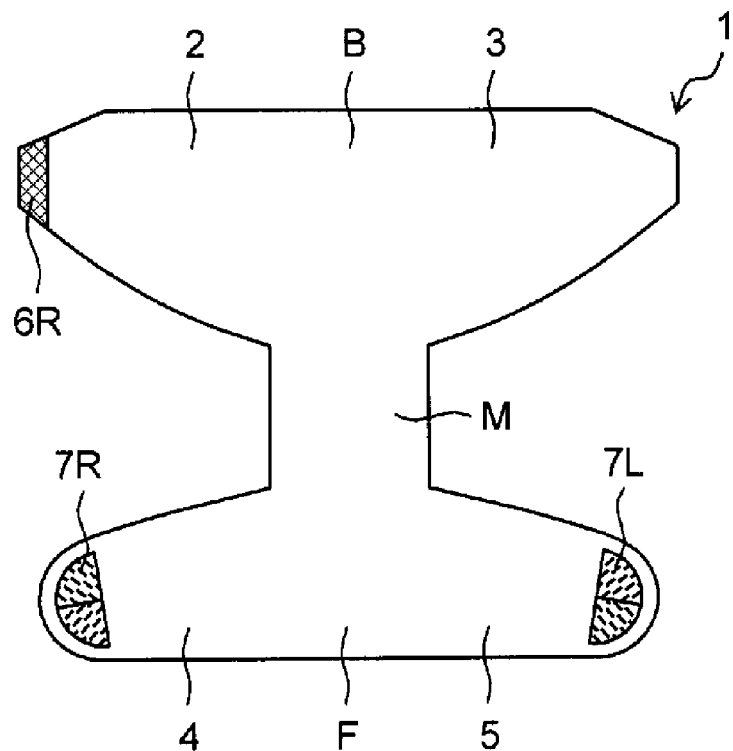
FIG. 2A shows an example of a wearing method of the diaper cover shown in FIG. 1, and shows the diaper cover in the state where the diaper cover is not worn and is spread in a plane.
Figure 2B:
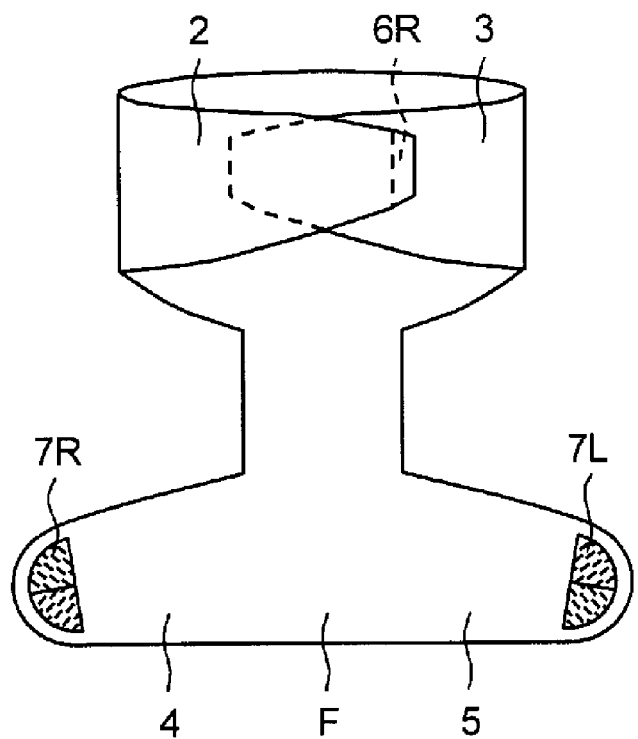
FIG. 2B shows an example of a wearing method of the diaper cover shown in FIG. 2A, and shows the diaper cover in the state where a right waist part and a left waist part are joined to each other.
Figure 2C:
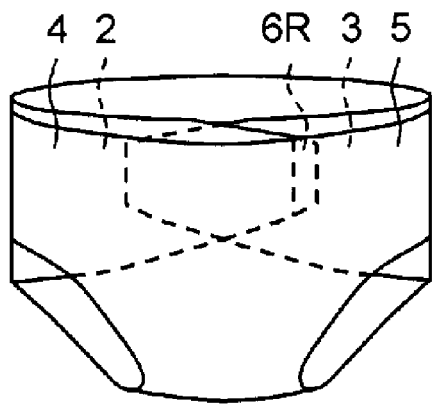
FIG. 2C shows an example of a wearing method of the diaper cover shown in FIG. 2B, and shows the diaper cover in the state where the diaper cover is worn.

An example of a wearing method of the diaper cover shown in FIG. 1 is explained with reference to FIGS. 2A to 2C. In the diaper cover 1 shown in FIGS. 2A to 2C, the right waist part 2, the left waist part 3 and the back part B are composed of a material to which the waist attachment 6 and the hook member 7 provided at the flap part are attachable. Hereinafter, the right flap part and/or the left flap part may be simply referred to as a flap part.

For wearing the diaper cover 1, firstly, while the back part B is in contact with the dorsal side of a wearer, the right waist part 2 is brought into contact with the right side of the waist of the wearer, and the left waist part 3 is brought into contact with the left side of the waist of the wearer. Secondly, the waist attachment 6R of the right waist part 2 is attached to the outer surface of the left waist part 3 while pulling the right waist part 2 (see FIGS. 2A and 2B). As a result, the right and left waist parts 2, 3 are fixed around the waist of the wearer. Thirdly, the front part F, the right flap part 4 and the left flap part 5 are brought through the crotch of the wearer to the abdomen side of the wearer; the right flap part 4 and the left flap part 5 are pulled in the upward direction of the wearer while being pulled in the right-left direction of the wearer; and the right flap part 4 and the left flap part 5 are attached to the right waist part 2, the left waist part 3 or the back part B with the hook members 7 (see FIGS. 2B and 2C). As a result, the diaper cover 1 can be worn. In FIG. 2C, the hook members 7 provided at the right and left flap parts 4, 5 are joined to a position on the dorsal side of the wearer; however, the hook members 7 may be joined to a position on an abdomen side of the wearer.

In wearing the diaper cover, the hook member provided at the flap part is often joined to a position about the pelvis (that is, the ilium, particularly the iliac crest or the like) of a wearer. In such a part of a human body, a great uneven or curved surface is found, and particularly, a great uneven or curved surface is formed with respect to the up-down direction of a wearer. Therefore, when the hook member is joined to such a position, the hook member is easily disjoined. In addition, in the state where the diaper cover is worn, forces acting in various directions, such as inward in the left-right direction of a wearer and the lower direction of the wearer, tend to be applied to the hook member of the flap part. Further, in accordance with movement or a body posture of the wearer, the orientation or magnitude of the force applied to the hook member is changed with frequency. As a result, the hook member joined to the right or left waist part or the like is further easily disjoined. These problems are rarely focused on in a so-called tape type diaper in which hook members are provided at both left and right ends on the back side of the diaper. This is because the hook members provided in the tape type diaper are joined to a relatively flat part on the abdomen side of a wearer.

Therefore, in the present invention, in order that joining (engaging) of the hook member provided at the flap part is less likely to be disjoined easily, the hook member has at least a first region and a second region, which are explained below in detail, and the first region and the second region are respectively oriented in particular directions.

Figure 3:
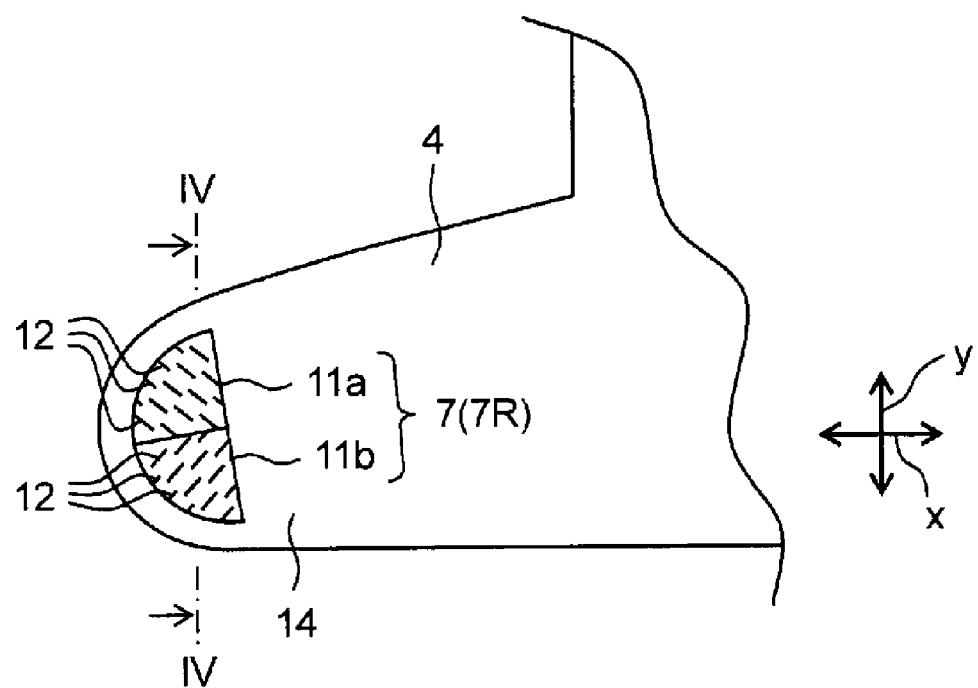
FIG. 3 shows an enlarged view of a flap part of the diaper cover shown in FIG. 1.

Details of the hook member 7 which is provided at the right flap part 4 and/or the left flap part 5 are explained in the following, with reference to FIGS. 3 and 4. FIG. 3 shows an enlarged view of the right flap part 4 of the diaper cover 1 shown in FIG. 1. FIGS. 4A and 4B show a cross sectional view along a line IV-IV in the right flap part 4 shown in FIG. 3. In FIGS. 4A and 4B, different embodiments of hook members 7R from each other are shown.

Figure 4A:
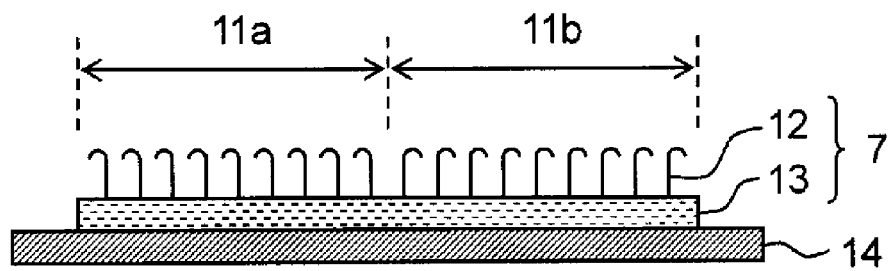
FIG. 4A shows one example of a cross sectional view along a line IV-IV in the flap part (a hook member) shown in FIG. 3.
Figure 4B:
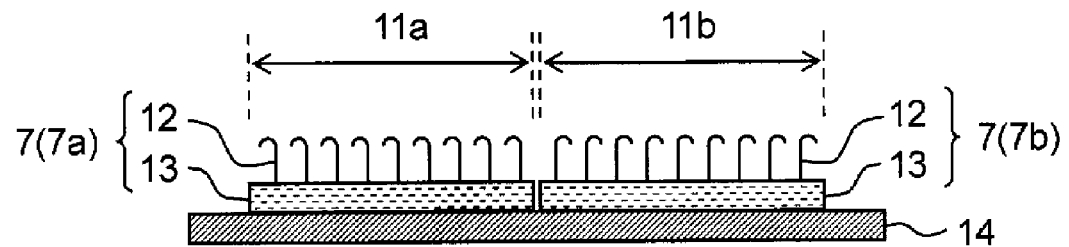
FIG. 4B shows another example of a cross sectional view along a line IV-IV in the flap part (a hook member) shown in FIG. 3.

In FIGS. 3 and 4A-B, the hook members 7 are provided on a main sheet 14 which forms the right flap part 4. The main sheet 14 forms, for example, the front part F, the intermediate part M, the back part B, the right waist part 2, the left waist part 3, the right flap part 4, and the left flap part 5. The hook member 7 includes, for example, a platform 13 and a plurality of hooks 12 projecting from the platform 13. The opposite surface of the surface with the hook 12 of the platform 13 is fixed to the main sheet 14.

In FIGS. 4A-B, the hook 12 has a dogleg shape. A shape of the hook is not limited to the dogleg shape, and may be an anchor shape, a mushroom shape, or the like. In the hook member 7, a plurality of pins serving as a part of the hooks 12 project from the platform 13, and an engagement part is provided at the top of the pin. The engagement part gives various shapes in accordance with the shape of the hook 12. For example, in a dogleg-shaped hook, the top of the pin bends in one direction. In an anchor-shaped hook, a crossbar is provided at the top of the pin as the engagement part. In the anchor-shaped hook, the crossbar does not necessarily have a rod shape, and any shape extending substantially point symmetrically with respect to the axis of the pin is allowed. In a mushroom-shaped hook, a cap is provided at the top of the pin as the engagement part. The cap preferably has an anisotropic shape such as having a long axis direction and a short axis direction. For example, the cap has an elliptical shape in a cross-section on a plane perpendicular to the axis of the pin. The anchor-shaped hook and the mushroom-shaped hook generally have a shape such that the engagement part is substantially point symmetrical with respect to axis of the pin.

The hook member 7 has at least a first region 11a and a second region 11b, and the hooks 12 in the first region 11a are oriented in one direction and the hooks 12 in the second region 11b are oriented in another direction. Thus, the plurality of hooks 12 provided in the first region 11a and the plurality of hooks 12 provided in the second region 11b are respectively oriented uniformly in respective regions; however, the orientation direction of hooks 12 in the first region 11a and the orientation direction of hooks 12 in the second region 11b are different from each other. In FIG. 3, the orientation directions of hooks 12 are presented in lines.

The hooks being oriented in one direction is explained as follows. When the hook member is seen in a plan view, that is, in the perpendicular direction to the platform, the tops of the hooks are aligned in one direction. For example, in the case of the dogleg-shaped hook, the tops of the hooks (the pins) bend in one direction. In the case of the anchor-shaped hook, the orientation directions of the crossbars provided at the tops of the pins are arranged in one direction. In the case of the mushroom-shaped hook, the orientation directions of the caps provided at the tops of the pins are arranged in one direction.

The first region 11a and the second region 11b are arranged in the right flap part 4 or the left flap part 5 so that a following hypothetical line is presented. That is, in the diaper cover 1, there exist a hypothetical straight line extending in the front-back direction in the right flap part 4 or the left flap part 5 and crossing both the first region 11a and the second region 11b. In FIG. 3, the line IV-IV extends in the front-back direction y in the right flap part 4 and crosses both the first region 11a and the second region 11b, and thus, the line IV-IV corresponds to the hypothetical line. The hypothetical line does not need to exist so as to be visible, and is commonly invisible.

As for an arrangement example of the first region 11a and the second region 11b, the first region 11a and the second region 11b may be disposed so as to be aligned in the front-back direction y, for example. The first region 11a and the second region 11b may be also arranged in the front-back direction y while being shifted in the width direction x, as long as there exist a crossover between the projected first region and the projected second region onto a line extending in the width direction. Thus, the first region 11a and the second region 11b may be arranged obliquely to the width direction x and the front-back direction y.

In the diaper cover of the present invention, since the hook member having the first region and the second region arranged in such a manner is provided in the flap part, joining (engaging) of the hook member is less likely to be disjoined easily when the diaper cover is worn. That is, since the hooks of the hook member are oriented in different directions between the first region and the second region, joining of both the first region and the second region are less likely to be disjoined at one time even when forces acting in various directions are applied to the hook member of the flap part. Further, in the diaper cover, since the first region and the second region are arranged such that the above-described hypothetical line is presented, the first region and the second region easily fit the uneven or curved surface of a wearer in the up-down direction of the wearer even when the hook member is joined to a position about the pelvis (that is, the ilium, particularly the iliac crest or the like) of the wearer. As a result, the first region and the second region can be suitably fixed to the right waist part, the left waist part, or the like. In addition, forces mainly acting inward in the width direction x and secondarily acting downward of a wearer (in the front-back direction y), tend to be applied to the hook member of the flap part when the diaper is worn; nevertheless, in the diaper cover of the present invention, since the first region and the second region are arranged such that the above-described hypothetical line is presented, both the first region and the second region can resist against such forces when such forces are actually applied to the hook member. Thus, since at least one of the first region and the second region can resist the force of releasing the hook member, the one of the first region and the second region suppresses disjoining of the other of them, so that the joining of the hook member is not easily disjoined.

The hook member may have a third region in addition to the first region and the second region. The orientation direction of the hooks in the third region may be the same as those in the first region or the second region, or may be different from those in the first region and the second region. Preferably, the hooks in the third region are oriented in a direction which is different from the orientation directions of the hooks in the first region and the second region. When the hooks in the third region are provided in such a manner, joining of the hook member is much less likely to be disjoined in wearing the diaper cover.

The hypothetical straight line extending in the front-back direction in the right flap part or the left flap part and crossing both the first region and the second region may further cross the third region or not. Preferably, there exist a hypothetical straight line extending in the front-back direction in the right flap part or the left flap part and crossing all of the first region, the second region and the third region. When the third region is provided such that a hypothetical line like this is presented, joining of the hook member is much less likely to be disjoined in wearing the diaper cover.

The hook member may further have a fourth region and other regions. However, description concerning the fourth region and other regions is omitted, since it is repetitive of the description of the third region.

A position where the hook member is provided in the flap part is not limited; however, the hook member is preferably provided within 100 mm (more preferably within 80 mm, and even more preferably within 50 mm) from the end of the flap part in the width direction x. When the hook member is provided in such a manner, the hook member can be joined to the right waist part, the left waist part, or the like while holding the ends, with respect to the width direction x, of the flap parts, in wearing the diaper cover. Thereby, the diaper can be easily worn. In addition, since the right and left flap parts are easily pulled in the right-left direction of a wearer while the ends, with respect to the width direction x, of the right and left flap parts being held, the fitting property of the diaper cover to the wearer is easily enhanced in wearing the diaper cover.

A shape of a region where the hook member is disposed on the right or left flap part and shapes of the first region and the second region are not particularly limited. These shapes may be a circular sectoral shape (including semicircular shape), which is shown in FIG. 1, a linear shape having a width, a quadrangular shape (including a quadrangular shape whose corners are rounded), an elliptical shape, a triangular shape (including a triangular shape whose corners are rounded), or the like.

The first region and the second region may be formed in one hook member or may be formed in different hook members. In FIG. 4A, the first region 11a and the second region 11b are formed in one hook member 7. On the other hand, in FIG. 4B, the first region 11a is formed in a hook member 7a and the second region 11b is formed in a hook member 7b which differs from the hook member 7a.

In order that all joining of the hook members are less likely to be disjoined at one time, the first region 11a and the second region 11b are preferably formed in different hook members 7a, 7b. Thus, the right flap part 4 and/or the left flap part 5 is preferably provided with the plurality of hook members 7 including a first hook member 7a having the first region 11a and a second hook member 7b having the second region 11b. In this case, the right flap part 4 and/or the left flap part 5 is provided with the first hook member 7a in which hooks 12 are oriented in one direction and the second hook member 7b in which hooks 12 are oriented in another direction. The hypothetical straight line crosses both the first hook member 7a and the second hook member 7b.

In the case where the respective regions are formed in different hook members, it is preferred that the hook members are separated from each other. That is, the first hook member 7a and the second hook member 7b are preferably separated from each other. The hook members generally have a certain degree of rigidity; and, when the hook members are provided so as to be separated from each other, a portion of the flap part where the hook members are disposed easily fits the uneven or curved surface of a wearer. In addition, even when joining of one of the hook members is disjoined; joining of the other hook member is not easily disjoined along with that. Therefore, all joining of the hook members provided in the flap part becomes less likely to be disjoined at one time. A distance (a shortest distance) between the separated hook members is preferably 0.5 mm or more, more preferably 1 mm or more, and preferably 10 mm or less, more preferably 7 mm or less.

Preferable embodiments of the hook member in the case where the respective regions are formed in different hook members are explained in the following, referring to FIGS. 5, 7, 9 and 11. FIGS. 5, 7, 9 and 11 show hook members 7R which are provided in the right flap part 4. In FIGS. 5, 7, 9 and 11, a first region 11a is formed in a first hook member 7a, a second region 11b is formed in a second hook member 7b, and a third region 11c is formed in a third hook member 7c. Further, in FIGS. 7, 9 and 11, a fourth region 11d is formed in a fourth hook member 7d.

Figure 5:
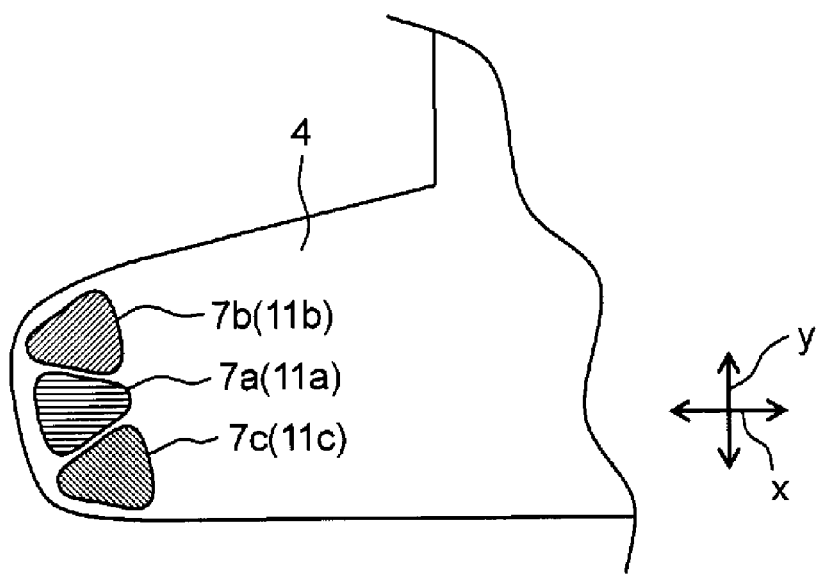
FIG. 5 shows one example of shape and arrangement of the hook member provided in the flap part.

FIG. 5 shows a preferred embodiment of the hook member, that is a first embodiment. As shown in FIG. 5, it is preferable that the first hook member 7a narrows inward in the width direction x in the right flap part 4 (or the left flap part 5), and the second hook member 7b narrows outward in the width direction x in the right flap part 4 (or the left flap part 5). In this case, since the first hook member 7a is formed such that the end side, with respect to the right or left flap part 4,5, is wider, the first hook member 7a can resist against a peeling force from the end side of the right or left flap part 4, 5 in wearing the diaper cover 1. Meanwhile, the second hook member 7b is formed such that the inner side, with respect to the width direction x, of the right or left flap part 4, 5 is wider, the second hook member 7b can resist a peeling force from the inner side of the right or left flap part 4, 5 in wearing the diaper cover 1. Therefore, even when the front part F of the diaper cover 1 is distorted or twisted due to a wearer's heavy movement, the second hook member 7b is less likely to be disjoined to the right and left flap part 4,5. In addition, since the first hook member 7a and the second hook member 7b can be arranged close to each other in an end part of the right or left flap part 4, 5 in the width direction x, the total area of the hook members 7 can be easily enlarged. As a result, a total joining force of the hook members 7 is easily improved.

In FIG. 5, the third hook member 7c is provided in addition to the first hook member 7a and the second hook member 7b. The third hook member 7c is preferably provided so as to narrow in the opposite direction to the adjacent hook member. In FIG. 5, since the third hook member 7c is adjacent to the first hook member 7a, the third hook member 7c preferably narrows outward in the width direction x. That is, in the case where three or more hook members are provided, the hook members are preferably respectively provided such that one of the adjacent hook members narrows inward in the width direction and the other of the adjacent hook members narrows outward in the width direction. Although not shown in FIG. 5, the same is applied to a case where the fourth hook member and other hook members are provided.

In the first embodiment, examples of the shape of the first hook member and the second hook member include a triangular shape (including a triangular shape whose corners are rounded), a trapezoidal shape (including a trapezoidal shape whose corners are rounded), a circular sectoral shape (including a circular sectoral shape whose corners are rounded), and the like. In FIG. 5, the shape of the first and second hook members is a triangle whose corners are rounded.

Figure 6:
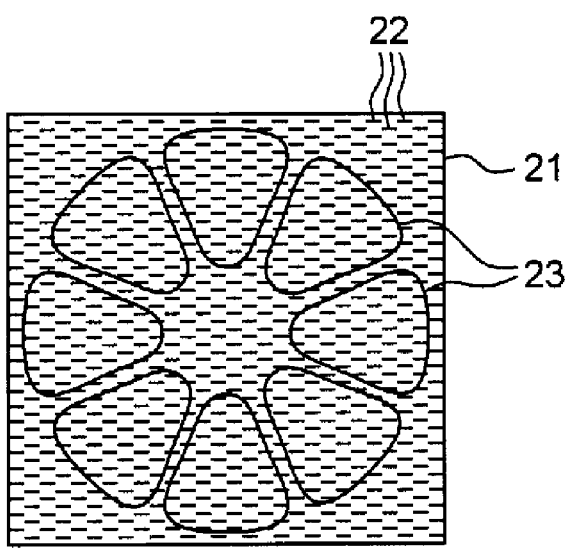
FIG. 6 shows an example of manufacturing the hook member shown in FIG. 5.

An example of manufacturing the first and second hook members shown in FIG. 5 is depicted FIG. 6. FIG. 6 shows a hook member sheet 21 in which a plurality of hooks 22 oriented in one direction, that is a right and left direction in the drawing, are provided. The first hook member and the second hook member are obtained by cutting out the hook member sheet 21 into, for example, triangle pieces 23 whose corners are rounded. In the hook member sheet 21, the triangle pieces 23 whose corners are rounded are arranged such that the plurality of triangle pieces 23 form a substantial circle, and the triangle pieces 23 arranged in such a manner are cut out from the hook member sheet 21. The thus obtained first hook member and the second hook member are disposed on the right flap part (or the left flap part) such that the triangle pieces whose corners are rounded narrow inward or outward in the width direction x in the right flap part (or the left flap part), thereby obtaining the right flap part as shown in FIG. 5.

In the above description concerning the first embodiment, though the first and second hook members are mainly explained, the same is applied to the third hook member and other hook members.

Figure 7:
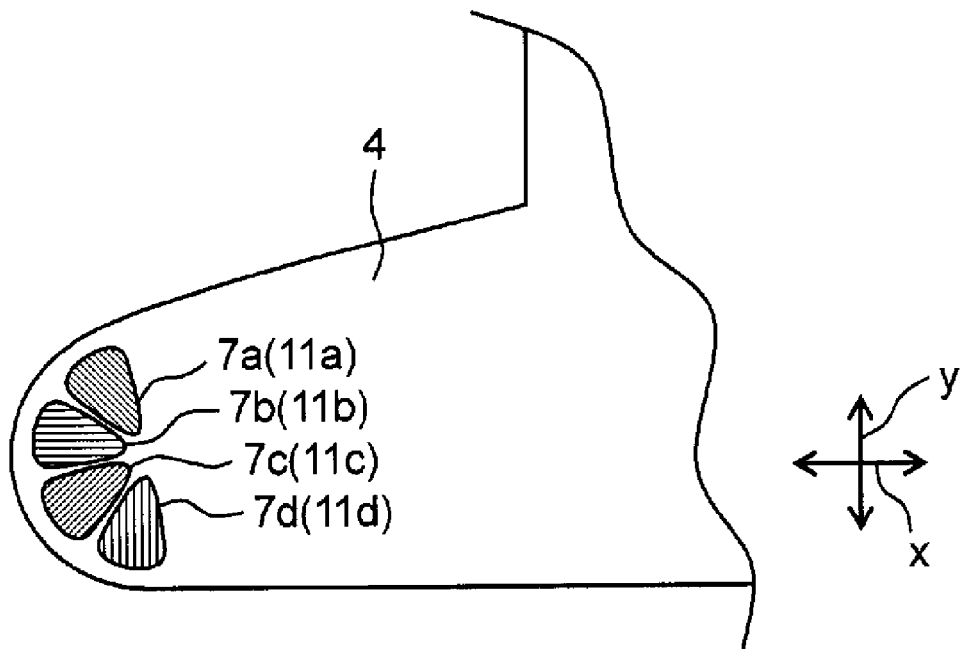
FIG. 7 shows another example of shape and arrangement of the hook member provided in the flap part.

FIG. 7 shows another preferred embodiment of the hook member, that is a second embodiment. As shown in FIG. 7, it is also preferable that each of the first hook member 7a and the second hook member 7b narrows inward from an edge of the right flap part 4 (or left flap part 5). In this case, since the first hook member 7a and the second hook member 7b are respectively formed such that the outer sides, with respect to the width direction x, of the right or left flap part 4,5 are wider, the first hook member 7a and the second hook member 7b can respectively resist a peeling force from the edge of the right or left flap part 4, 5 in wearing the diaper cover 1, and therefore, joining of each of the first hook member 7a and the second hook member 7b is strengthened. In addition, since the first hook member 7a and the second hook member 7b can be arranged close to each other in the end part of the right or left flap part 4, 5 in the width direction x, the total area of the hook members 7 can be easily enlarged. As a result, a total joining force of the hook members 7 is easily improved.

In FIG. 7, the third hook member 7c and the fourth hook member 7d are provided in addition to the first hook member 7a and the second hook member 7b; and it is also preferable that each of the third hook member 7c and the fourth hook member 7d narrows inward from the edge of the right flap part 4 (or left flap part 5). Although not shown in FIG. 7, the same is applied to a case where a fifth hook member and other hook members are provided.

As the shape of the first and second hook members used in the second embodiment, the shape of the hook member which can be employed in the first embodiment may be employed. In FIG. 7, the shape of the first and second hook members is a circular section whose corners are rounded.

In the case where the first hook member and the second hook member are disposed so as to narrow inward from the edge of the right or left flap part, the hooks provided on the first hook member and the second hook member are preferably oriented toward the edge of the right flap part or the left flap part. That is, for example, in the dogleg-shaped hook, the tops of the hooks bend preferably toward the edge of the right or left flap part. In the anchor-shaped hook, the longitudinal directions of the crossbars provided at the tops of the pins are preferably oriented toward the edge of the right or left flap part. In the mushroom shape hook, the long axes of the caps provided at the tops of the pins are preferably oriented toward the edge of the right or left flap part. When the hook members are oriented in such a manner, the first hook member and the second hook member tend to be joined more strongly to the right waist part, the left waist part or the like in wearing the diaper cover.

Figure 8:
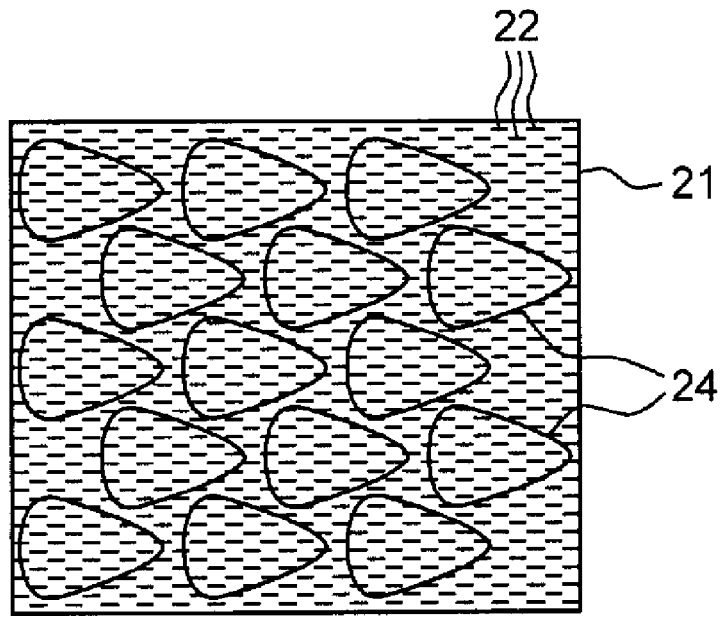
FIG. 8 shows an example of manufacturing the hook member shown in FIG. 7.

An example of manufacturing the first and second hook members shown in FIG. 7 is depicted FIG. 8. FIG. 8 shows a hook member sheet 21 provided with a plurality of hooks 22 oriented in one direction, which is a right and left direction in the drawing. The first hook member and the second hook member are obtained by cutting out the hook member sheet 21 into, for example, circular sectors 24 whose corners are rounded. In the hook member sheet 21, the circular sectors 24 whose corners are rounded are arranged so as to be oriented in one direction, and the circular sectors 24 whose corners are rounded arranged in such a manner are cut out from the hook member sheet 21. The thus obtained first hook member and the second hook member are disposed on the right flap part (or the left flap part) such that the circular sectors 24 whose corners are rounded narrow inward from the edge of the right flap part (or the left flap part), thereby obtaining the right flap part as shown in FIG. 7. According to a manufacturing example shown in FIG. 8, the hooks provided on the first hook member and the second hook member come to be oriented toward the edge of the right flap part or the left flap part.

Figure 9:
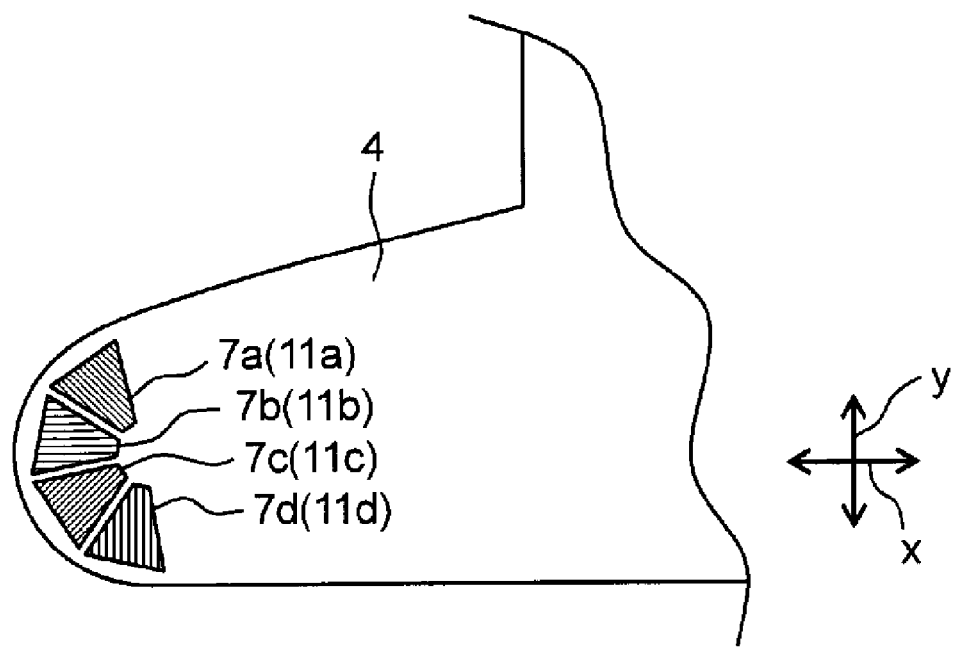
FIG. 9 shows still another example of shape and arrangement of the hook member provided in the flap part.

FIG. 9 shows an embodiment in which the shape of the first hook member and the second hook member is different from that in FIG. 7. In FIG. 9, the shape of the first hook member and the second hook member is trapezoid. In the case where the shape of the first hook member and the second hook member is trapezoid as shown in FIG. 9, the hook member sheet generates less waste when the hook members are cut out from the hook member sheet. This effect is obtained particularly in the case where the shape of the engagement part is substantially point symmetrical with respect to the axis of the pin as in the anchor-shaped hook and the mushroom-shaped hook in the second embodiment. Similar effect is obtained in the case where the shape of the first hook member and the second hook member is not only trapezoid but also triangle. This is explained in the following with reference to FIG. 10.

Figure 10:
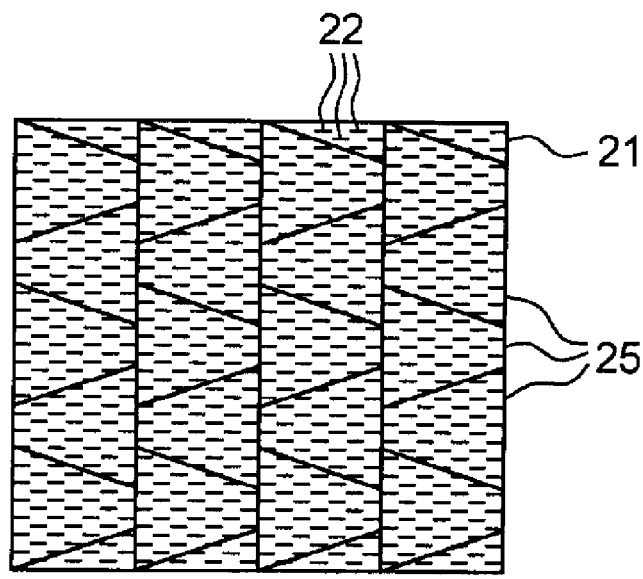
FIG. 10 shows an example of manufacturing the hook member shown in FIG. 9.

An example of manufacturing the first and second hook members shown in FIG. 9 is depicted in FIG. 10. FIG. 10 shows a hook member sheet 21 provided with a plurality of hooks 22 oriented in one direction, which is a right and left direction in the drawing. In the hook member sheet 21, a plurality of trapezoids 25 are arranged so as to be alternately changed in the up-down direction (with respect to the upper and lower sides of the trapezoid), and the adjacent trapezoid pieces 25 are not separated from each other. The first hook member and the second hook member are obtained by cutting out the hook member sheet 21 into trapezoids 25. Thus, in the case where the shape of the first hook member and the second hook member is trapezoid, the hook member sheet 21 can generate less waste.

In the above description concerning the second embodiment, though the first and second hook members are mainly explained, the same is applied to the third hook member and other hook members.

Figure 11:
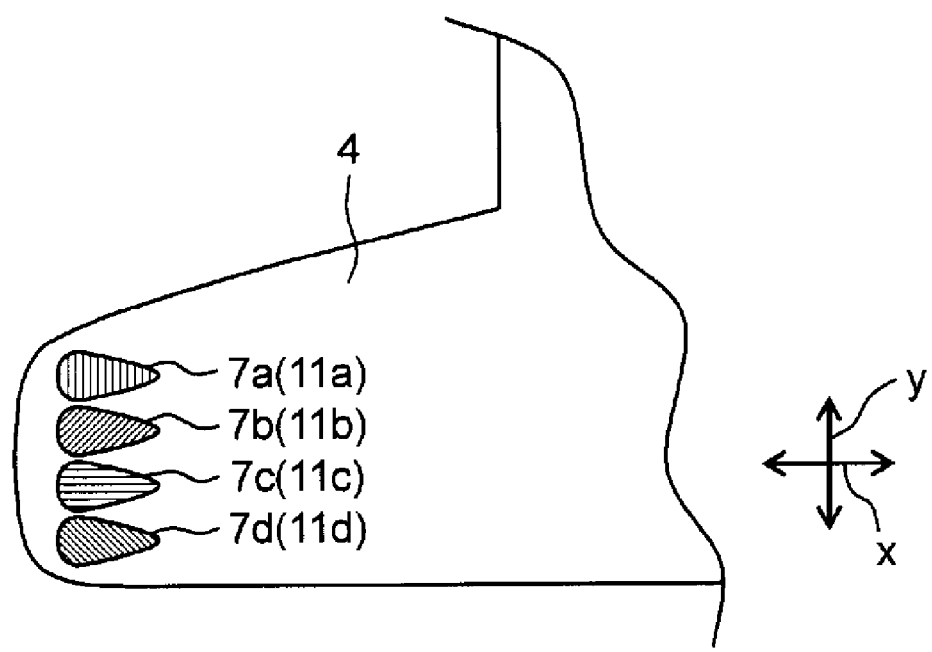
FIG. 11 shows still another example of shape and arrangement of the hook member provided in the flap part.

FIG. 11 shows further another preferred embodiment of the hook member, which is a third embodiment. As shown in FIG. 11, it is also preferable that each of the first hook member 7a and the second hook member 7b narrows inward in the width direction x of the right flap part 4 (or left flap part 5). In this case, since the first hook member 7a and the second hook member 7b are respectively formed such that the end sides, with respect to the right or left flap part 4,5, are wider, the first hook member 7a and the second hook member 7b can respectively resist a peeling force from the end side of the right or left flap part 4, 5 in wearing the diaper cover 1, and therefore, joining of each of the first hook member 7a and the second hook member 7b is strengthened. Moreover, since the first hook member 7a and the second hook member 7b narrow inward in the width direction x, flexibility and stretchability of the main sheet are less likely to be inhibited by the hook member 7 at the inner side, with respect to the width direction x, of the right or left flap part 4,5, thereby improving handleability of the diaper cover.

In FIG. 11, the third hook member 7c and the fourth hook member 7d are provided in addition to the first hook member 7a and the second hook member 7b; and it is also preferable that each of the third hook member 7c and the fourth hook member 7d narrows inward in the width direction x of the right flap part 4 (or the left flap part 5). Although not shown in FIG. 11, the same is applied to a case where the fifth hook member and other hook members are provided.

As the shape of the first and second hook members used in the third embodiment, the shape of the hook member which can be employed in the first embodiment may be employed. In FIG. 11, the shape of the first and second hook members is a circular section whose corners are rounded. For manufacturing the first and second hook members shown in FIG. 11, the method shown in FIG. 6 can be employed.

In the above description concerning the third embodiment, though the first and second hook members are mainly explained, the same is applied to the third hook member and other hook members.

In the above description, the embodiment in which each of the right flap part 4 and the left flap part 5 is provided with the hook member 7 having the first region 11a and the second region 11b is explained; however, it is only necessary that at least one of the right flap part 4 and the left flap part 5 is provided with the hook member 7 having the first region 11a and the second region 11b. For example, either of the right flap part 4 or the left flap part 5 may be provided with a hook member having only the first region. Alternatively, either of the right flap part 4 or the left flap part 5 may be provided with an adhesive (e.g., an adhesive tape and an adhesive layer). However, in the present invention, each of the right flap part 4 and the left flap part 5 is preferably provided with the hook members 7 having the first region 11a and the second region 11b.

The waist attachment 6 is explained in the following, referring to FIG. 1. The waist attachment 6R of the right waist part 2 is preferably provided so as to be attachable to the left waist part 3 or the back part B. Also, the waist attachment 6L of the left waist part 3 is preferably provided so as to be attachable to the right waist part 2 or the back part B, although not shown in FIG. 1. For improving handleability of the right and left waist parts 2, 3, the waist attachment 6R is preferably provided so as to be attachable to the left waist part 3, and the waist attachment 6L is preferably provided so as to be attachable to the right waist part 2.

For example, the waist attachment 6 may be provided on the inner surface of the right and left waist parts 2, 3. In this case, the waist attachment 6 is attachable to the outer surface of the right waist part 2 or the left waist part 3, thereby improving handleability of the right and left waist parts 2, 3. Alternatively, the waist attachment 6R may be provided on the inner surface of the right waist part 2 and the waist attachment 6L may be provide on the outer surface of the left waist part 3. In this case, for wearing the diaper cover, the waist attachment 6L is attached to the inner surface of the right waist part 2, and then the waist attachment 6R is attached to the outer surface of the left waist part 3 while overlapping the left waist part 3 with the right waist part 2, whereby the right and left waist parts can be easily fixed around the waist of a wearer stably. Of course, the surfaces of the right and left waist parts 2, 3 where the waist attachments 6R, 6L are provided may be reversed between the inner and outer surfaces. Still alternatively, the waist attachment 6 may be provided so as to extend from the end of the right waist part 2 or the left waist part 3 in the width direction x. For improving handleability of the right and left waist parts 2, 3, the waist attachment 6 is preferably provided at least on the inner surface of the right waist part 2 and/or the inner surface of the left waist part 3.

In the case where the waist attachment 6 is provided on the inner surface of the right and left waist parts 2, 3, the waist attachment 6 is preferably provided within 100 mm (more preferably within 80 mm, and even more preferably within 50 mm) from the end of the right or left waist part 2, 3 in the width direction x. When the waist attachments 6 are provided in such a manner, the waist attachments 6 can be joined to the right waist part 2, the left waist part 3 or the back part B while holding the ends, with respect to the width direction x, of the right waist part 2 and the left waist part 3, whereby the diaper cover 1 is easily worn.

Examples of the waist attachment include a hook member and a loop member of a hook-and-loop fastener, an adhesive (e.g., an adhesive tape and an adhesive layer), a hook (e.g., a metallic hook and a plastic hook), and the like. Among them, a hook member of a hook-and-loop fastener is preferably used as the waist attachment. As the hook member, a member in which many hooks of, for example, an anchor shape, a dogleg shape, a mushroom shape, or the like are provided on the surface thereof can be employed. A hook member which can be used for the hook member provided in the flap part may be provided.

A shape of the waist attachment, that is a shape of a region where the waist attachment is disposed in the right or left waist part 2, 3, is not particularly limited. For example, it is preferred that the shape of the waist attachment is long in the front-back direction y, and the waist attachment 6R having such shape is provided at the right waist part 2 in FIG. 1. The waist attachment having the shape long in the front-back direction y means that the length of the waist attachment in the front-back direction y is longer than that in the width direction x. The waist attachment is not necessarily provided so as to be parallel to the front-back direction y, and may be provided obliquely with respect to the front-back direction y. When the waist attachment has the shape that is long in the front-back direction y, the right and left waist parts can be widely joined, and thus tend to be stably fixed around the waist of a wearer. Examples of the shape of the waist attachment include, for example, a linear shape, an elliptical shape, a quadrangular shape (including a quadrangular shape whose corners are rounded), a triangular shape (including a triangular shape whose corners are rounded), a circular sectoral shape (including a circular sectoral shape whose corners are rounded), and the like.

For enhancing the fitting property of the diaper cover 1 around the waist of a wearer, the right flap part 4, the left flap part 5 and the intermediate part M are preferably stretchable. The edges of these parts are applied to about an inguinal region of a wearer in wearing the diaper cover 1. Therefore, when the diaper 1 is stretchable at these parts, the fitting property of the diaper cover around the legs of a wearer is easily improved by fixing the right and left flap parts 4, 5 around the waist of the wearer while the right and left flap parts 4, 5 are expanded in the right-left direction of the wearer and are pulled in the upward direction of the wearer. It is further preferred that the front part F is also stretchable in addition to the right flap part 4, the left flap part 5 and the intermediate part M.

In the diaper cover 1, the right waist part 2 and the left waist part 3 are preferably stretchable. In detail, the right waist part 2 and the left waist part 3 are preferably stretchable in the width direction x. When the right waist part 2 and the left waist part 3 are stretchable, the fitting property of the diaper cover around the waist of a wearer is easily improved by fixing the right and left waist parts 2, 3 around the waist of the wearer while the right and left waist parts 2, 3 are expanded.

It is further preferred that the front part B is also stretchable in addition to the right waist part 2 and the left flap part 3.

A material constituting the diaper cover, that is, a material of the main sheet, is not particularly limited. Examples of the material constituting the diaper cover include a nonwoven fabric, a woven fabric, a knitted fabric, a plastic film, a laminate thereof, and the like. In the case that fabrics such as a nonwoven fabric, a woven fabric and a knitted fabric are used as the material constituting the diaper cover, synthetic fibers such as polypropylene, polyethylene, polyesters, polyamides and polyurethanes; or natural fibers such as pulp and silk may be used as fibers constituting the fabric, for example. In the case that a plastic film is used as the material constituting the diaper cover, synthetic resins such as polypropylene, polyethylene, polyesters, polyamides and polyurethanes may be used. The diaper cover may be either liquid-permeable or liquid-impermeable.

In the diaper cover, it is preferred that a loop member of a hook-and-loop fastener is provided at the right and left waist parts and/or the back part, or the right and left waist parts and/or the back part are composed of a material which functions as the loop member, such as a nonwoven fabric, a woven fabric, a knitted fabric or the like. When the right and left waist parts and/or the back part are composed of such a material, the hook member provided at the flap part can be fixed to the right and left waist parts and/or the back part in wearing of the diaper cover.

When the diaper cover has a part which is stretchable, that may be hereinafter referred to as "a stretchable part", the stretchable part is not particularly limited, as long as the stretchable part deforms with respect to a tensile load and generates force to return from its deformed shape to its original shape. The stretchable part preferably returns substantially to its original length even when being stretched at least 1.1-fold (more preferably 1.2-fold, even more preferably 1.5-fold), and preferably does not have a yield point in the above stretching range.

The stretchable part may be composed of a stretchable material. Examples of the stretchable material include natural rubbers; synthetic rubbers such as styrenebutadiene copolymer and polyisobutylene; synthetic resins such as polyurethanes, polyether-polyester, polybutylene terephthalate and poly trimethylene terephthalate; and the like. A nonwoven fabric, a woven fabric, a knitted fabric or the like which is composed of fibers containing the stretchable material may be used for the stretchable part. Alternatively, a film which the stretchable material is formed into may be used for the stretchable part.

The stretchable part may be composed of a non-stretchable material. In this case, a woven fabric, a knitted fabric or the like which are composed of fibers formed from the non-stretchable material and is imparted with a stretching property by a weaving or knitting method, may be used for the stretchable part.

The stretchable part may be composed of the stretchable material and the non-stretchable material. In this case, to a part which is non-stretchable and is composed of a non-stretchable material, which may be hereinafter referred to as "a non-stretchable part", a stretchable material such as an elastic member and the like may be attached. The stretchable material is preferably attached to the non-stretchable part in a stretched state. Further, a nonwoven fabric, a woven fabric, a knitted fabric or the like which is composed of fibers formed from the stretchable material and fibers formed from the non-stretchable material, or which are composed of composite fibers formed from the stretchable material and the non-stretchable material, may be used for the stretchable part.

The entire diaper cover except the hook member provided at the flap part and the waist attachment (when being provided), may be stretchable. In this case, the diaper cover is preferably composed of uniform material except the hook member provided at the flap part and the waist attachment, in view of easily manufacturing of the diaper cover.

For ensuring breathability of the diaper cover and lowering moisture therein during wearing, the diaper cover is preferably composed of a nonwoven fabric, a woven fabric, a knitted fabric or the like. More preferably, the entire diaper cover except the hook member and the waist attachment (when being provided), is composed of a nonwoven fabric, a woven fabric, a knitted fabric or the like.

The present invention also provides a disposable diaper in which an absorbent core is provided at the intermediate part of the diaper cover of the present invention. Thus, the disposable diaper of the present invention comprises a front part, a back part and an Intermediate part located between the front part and the back part in a front-back direction, a right waist part and a left waist part extending from the back part in a width direction, and a right flap part and a left flap part extending from the front part in the width direction, wherein: an absorbent core is provided at the intermediate part; the right flap part and/or the left flap part is provided with a hook member having a plurality of hooks; the hook member has a first region in which the hooks are oriented in one direction and a second region in which the hooks are oriented in another direction; and the first region and the second region are arranged such that a hypothetical straight line extending in the front-back direction in the right flap part or the left flap part crosses both the first region and the second region.

For example, the disposable diaper may comprise: an exterior sheet having a front part, a back part and an intermediate part located therebetween in a front-back direction, a right waist part and a left waist part extending from the back part in a width direction, and a right flap part and a left flap part extending from the front part in the width direction; and an absorbent main body including a liquid-permeable top sheet, a liquid-impermeable back sheet and an absorbent core interposed therebetween; wherein the absorbent main body is provided at the intermediate part of the exterior sheet. The exterior sheet may be composed of one sheet or may be formed by laminating two or more sheets. The exterior sheet includes, for example, a laminate of an inner sheet and an outer sheet. Here, the inner sheet is preferably hydrophilic or water-repellent, and the outer sheet is preferably water-repellent. The exterior sheet may have a stretchable part and a non-stretchable part.

Alternatively, the disposable diaper may comprise a laminate including a liquid-permeable top sheet, a liquid-impermeable back sheet and an absorbent core interposed therebetween, wherein the laminate has a front part, a back part and an intermediate part located therebetween in a front-back direction, a right waist part and a left waist part extending from the back part in a width direction, and a right flap part and a left flap part extending from the front part in the width direction, and the absorbent core is provided at the intermediate part. The laminate may have a stretchable part and a nonstretchable part. Still alternatively, a laminate in which an absorbent core is interposed between a liquid-permeable top sheet and a liquid-impermeable back sheet may form a non-stretchable part, and the remaining parts composed of a material which is different from materials of the top sheet and the back sheet may form a stretchable part.

The absorbent core is not particularly restricted as long as it absorbs excrement such as urine and the like. As the absorbent core, a clump of an absorbent material, which is formed into a predefined shape, may be used, or an absorbent material wrapped with a covering sheet such as paper (for example, tissue paper), a liquid-permeable nonwoven fabric and the like may be used, for example. Examples of the absorbent material contained in the absorbent core include, for example, a hydrophilic fiber such as a crushed pulp fiber and a cellulose fiber; and an absorbent polymer such as polyacrylic absorbent polymer, cellulosic absorbent polymer, and stark-acrylonitrile absorbent polymer. The absorbent material preferably contains at least an absorbent polymer. Further, the absorbent material may be obtained by mixing an absorbent polymer with a hydrophilic fiber assembly, or dispersing an absorbent polymer on a hydrophilic fiber assembly. A shape of the absorbent core is not limited. Examples of the shape of the absorbent core include a rectangular shape, an hourglass shape, a center nipped-in gourd shape, a battledore shape and the like.

The top sheet and the back sheet may be composed of a nonwoven fabric, a woven fabric, a knitted fabric, a plastic film, a laminate of a plastic film and a nonwoven fabric, or the like. Examples of the laminate include a laminate in which a sheet of a nonwoven fabric and a sheet of a plastic film are stacked, and a laminate in which a plastic film is interposed between nonwoven fabrics.

Examples of the top sheet include, for example, a nonwoven fabric formed from hydrophilic fibers such as cellulose and rayon; and a nonwoven fabric which is formed from hydrophobic fibers such as polypropylene, polyethylene, polyester, polyamide and nylon, and in which the hydrophobic fibers are hydrophilized with a surfactant on the surface thereof. As the top sheet, a woven fabric, a knitted fabric, a plastic film having pores may be also used.

Examples of the back sheet include, for example, a nonwoven fabric formed from hydrophobic fibers such as polypropylene, polyethylene, polyester, polyamide and nylon; and a plastic film. As the back sheet, a laminate of a nonwoven fabric and a plastic film may be also used.

As the exterior sheet, a material which can be used for the back sheet is preferably used in the case that the exterior sheet is composed of one sheet. In the case that the exterior sheet comprises the inner sheet and the outer sheet, a material which can be used for the top sheet or the back sheet may be used as the inner sheet, and a material which can be used for the back sheet may be used as the outer sheet.

When a nonwoven fabric is used for the sheet member explained above, a nonwoven fabric manufactured by a spunbonding method, an air-through method, a point bonding method, a melt blowing method, an airlaid method, a combination of these methods, or the like, is preferably used. Also, a nonwoven fabric manufactured by an SMS method which is a combination of the spunbonding method and the melt blowing method may be used.

The disposable diaper preferably comprises rising flaps disposed at opposite sides of the absorbent core. For example, the rising flaps may be provided on an upper surface of the absorbent core at both sides in the width direction, or may be provided outside the absorbent core in the width direction. The rising flaps prevent lateral leakage of urine and the like. The rising flaps may be formed by rising inner edges of side sheets joined to opposite sides of the top sheet in the width direction. The rising flap and the side sheet are preferably water-repellent.

Descriptions concerning the right waist part, the left waist part, the right flap part, the left flap part, the waist attachment, and the hook member provided at the flap part are the same as those in the diaper cover.

Figure 12:
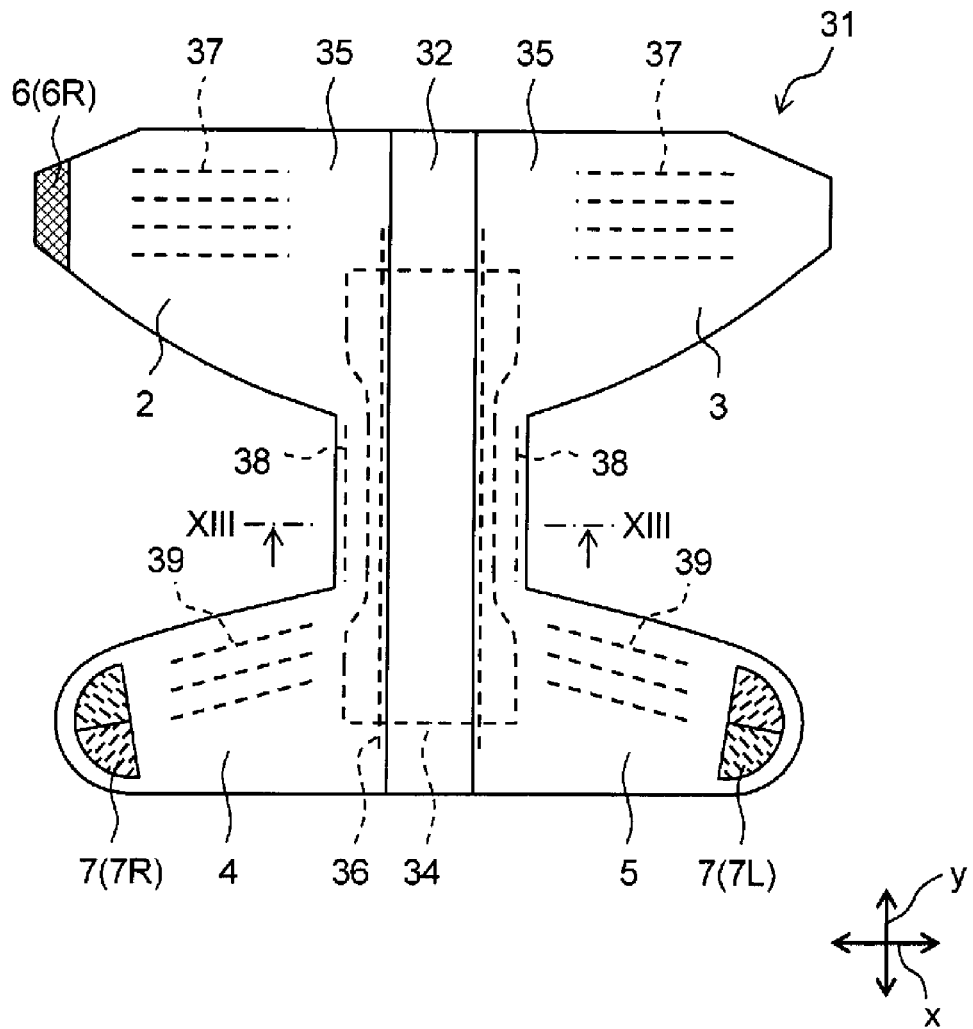
FIG. 12 shows one embodiment of a disposable diaper of the present invention.
Figure 13:
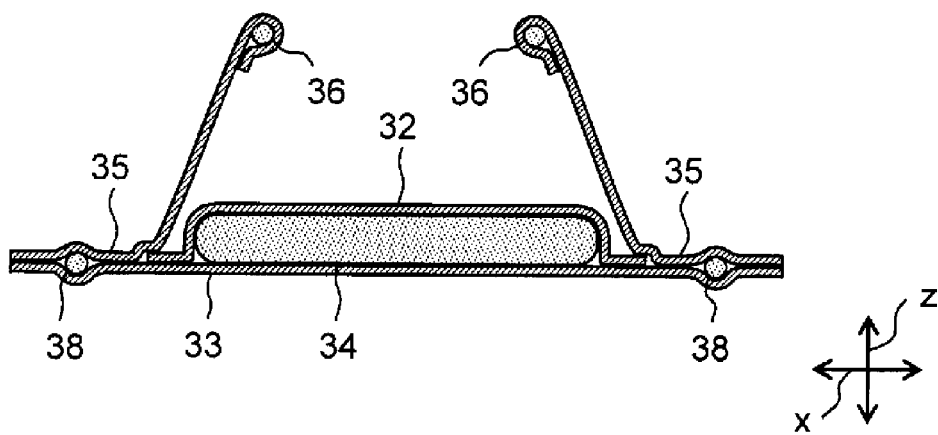
FIG. 13 shows a cross-sectional view taken along line XIII-XIII in the disposable diaper shown in FIG. 12.

An example of the disposable diaper of the present invention is explained in the following, referring to FIGS. 12 and 13. FIG. 12 shows an example of the disposable diaper of the present invention, and FIG. 13 shows a cross-sectional view taken along line XIII-XIII in FIG. 12. However, the disposable diaper of the present invention is not restricted to the following embodiment. In the following, description of the part overlapping the above description of the diaper cover is omitted. Further, the terms "diaper cover" and "diaper cover 1" in the above description of the diaper cover are respectively replaced with the terms "disposable diaper" and "disposable diaper 31".

A disposable diaper 31 comprises a laminate in which an absorbent core 34 is interposed between a liquid-permeable top sheet 32 and a liquid-impermeable back sheet 33. The top sheet 32 has a rectangular shape such that length in the width direction x is shorter than length in the width direction x of the intermediate part, and length in the front-back direction y is the substantially same as length in the front-back direction y of the disposable diaper 31. The back sheet 33 forms the front part, the back part and the intermediate part located therebetween in the front-back direction y, the right waist part 2 and the left waist part 3 extending from the back part in the width direction x, and the right flap part 4 and the left flap part 5 extending from the front part in the width direction x. Side sheets 35 are joined to both ends of the top sheet 32 in the width direction x, and the side sheets 35 forms the right waist part 2, the left waist part 3, the right flap part 4 and the left flap part 5.

The top sheet 32 is placed so as to face a wearer's skin, and allows excrement such as urine and the like to permeate through. The excrement that permeated the top sheet 32 is accommodated in the absorbent core 34. The back sheet 33 prevents the excrement from permeating outside, thereby protecting clothes and the like from becoming soiled.

A rising elastic member 36 is disposed at an inner end, with respect to the width direction x, of the side sheet 35. When the disposable diaper 31 is worn, the inner part of the side sheet 35 rises above the top sheet 32 due to a shrinkage force of the rising elastic member 36. Thus, the inner part of the side sheet 35 rises toward a wearer's skin to form a rising flap, thereby preventing excrement such as urine and the like from leaking outward in the width direction x.

Waist elastic members 37 extending in the width direction x are disposed in the right and left waist parts 2, 3. Parts of the right and left waist parts 2, 3 where the waist elastic members 37 are disposed function as the stretchable parts.

Leg elastic members 38 extending in the front-back direction y are disposed the Intermediate part. The elastic member 38 is disposed in the intermediate part along the edge of the disposable diaper 31. Flap elastic members 39 approximately extending in the width direction x are disposed in the right and left flap parts 4, 5. The leg elastic member 38 and the flap elastic member 39 improve the fitting property around the legs of a wearer.

The waist elastic member 37, the leg elastic member 38 and the flap elastic member 39 are respectively disposed between the side sheet 35 and the back sheet 33, and are fixed to side sheet 35 and the back sheet 33 in stretched states. Elastic materials such as a polyurethane thread, a polyurethane film, a natural rubber and the like, which are generally used for disposable diapers, can be used for the respective elastic members. The respective elastic members are preferably fixed in stretched states with a hot-melt adhesive. For example, a polyurethane thread having a fineness of 100 dtex to 2,500 dtex is stretched at a ratio of 1.1 to 5.0 times to be fixed. A preferable fixing means is a rubber hot-melt adhesive.

REFERENCE SIGNS LIST

1: a diaper cover
2: a right waist part
3: a left waist part
4: a right flap part
5: a left flap part
6: a waist attachment
7: a hook member
11a: a first region
11b: a second region
12: a hook
31: a disposable diaper

The invention claimed is:

1. A diaper cover comprising a front part, a back part and an intermediate part located between the front part and the back part in a front-back direction, a right waist part and a left waist part extending from the back part in a width direction, and a right flap part and a left flap part extending from the front part in the width direction,
wherein the right flap part and/or the left flap part is provided with a plurality of hook members including a first hook member in which all hooks project from a first platform and are oriented in one direction and a second hook member in which all hooks project from a second platform and are oriented in another direction,
wherein the first platform and the second platform are separated from each other, and
wherein the first hook member and the second hook member are arranged such that a hypothetical straight line extending in the front-back direction in the right flap part or the left flap part crosses both the first hook member and the second hook member.

2. The diaper cover according to claim 1, wherein the first hook member narrows in the inward width direction of the right or left flap part, and the second hook member narrows in the outward width direction of the right or left flap part.

3. The diaper cover according to claim 1, wherein each of the first hook member and the second hook member narrows inward from an edge of the right or left flap part.

4. The diaper cover according to claim 1, wherein each of the first hook member and the second hook member narrows inward in the width direction in the right or left flap part.

5. The diaper cover according to claim 1, wherein the first hook member and the second hook member are separated from each other.

6. The diaper cover according to claim 1, wherein the right flap part, the left flap part and the intermediate part are stretchable.

7. The diaper cover according to claim 1, wherein one or both of the right waist part and the left waist part is provided with a waist attachment.

8. A disposable diaper comprising;
the diaper cover according to claim 1, and
an absorbent core provided at the intermediate part of the diaper cover.

* * * * *